(12) United States Patent
Ogasawara et al.

(10) Patent No.: US 9,033,018 B2
(45) Date of Patent: May 19, 2015

(54) APPARATUS FOR MANUFACTURING ABSORBENT BODY

(75) Inventors: Yoshikazu Ogasawara, Kagawa (JP); Takanori Yano, Kagawa (JP); Kazuyo Miyazaki, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 13/980,382

(22) PCT Filed: Jan. 13, 2012

(86) PCT No.: PCT/JP2012/050588
§ 371 (c)(1),
(2), (4) Date: Sep. 26, 2013

(87) PCT Pub. No.: WO2012/099014
PCT Pub. Date: Jul. 26, 2012

(65) Prior Publication Data
US 2014/0008024 A1    Jan. 9, 2014

(30) Foreign Application Priority Data
Jan. 19, 2011   (JP) .................. 2011-009077

(51) Int. Cl.
*B31F 1/07*     (2006.01)
*A61F 13/00*    (2006.01)
*A61F 13/15*    (2006.01)

(52) U.S. Cl.
CPC ..... *A61F 13/00991* (2013.01); *A61F 13/15617* (2013.01)

(58) Field of Classification Search
CPC ................. A61F 13/15617; A61F 13/00991
USPC ............... 156/196, 199, 209, 210, 470–473
See application file for complete search history.

(56) References Cited

U.S. PATENT DOCUMENTS

| 4,610,678 A * | 9/1986 | Weisman et al. ............. 604/368 |
| 5,429,788 A * | 7/1995 | Ribble et al. .................. 264/510 |
| 2012/0056347 A1* | 3/2012 | Taniguchi et al. ............ 264/101 |

FOREIGN PATENT DOCUMENTS

| JP | 63283777 A | 11/1988 |
| JP | 07289589 A | 11/1995 |

(Continued)

OTHER PUBLICATIONS

International Search Report issued in PCT/JP2012/050588, dated Apr. 3, 2012, with English translation.

(Continued)

*Primary Examiner* — Mark A Osele
*Assistant Examiner* — Christopher C Caillouet
(74) *Attorney, Agent, or Firm* — Lowe Hauptman & Ham, LLP

(57) ABSTRACT

An apparatus for manufacturing an absorbent body includes: a suction member for moving a suction section along a predetermined travel path; a cover member surrounding a predetermined range of the travel path; and a supply opening through which liquid absorbent particles fall. The supply opening is provided above the travel path in a space within the cover member. Of the space within the cover member, a space located in a downstream side of a position of the supply opening in a direction along the travel path is divided into a first zone in which the liquid absorbent particle is suctioned to the suction section and a second zone in which the liquid absorbent particle is suctioned to the suction section, the second zone being adjacent to a downstream side of the first zone.

7 Claims, 6 Drawing Sheets

(56) References Cited

FOREIGN PATENT DOCUMENTS

| | | |
|---|---|---|
| JP | 11222208 A | 8/1999 |
| JP | 2002000650 A | 1/2002 |
| JP | 2003237921 A | 8/2003 |
| JP | 2006115999 A | 5/2006 |
| JP | 2008154605 A | 7/2008 |
| JP | 2009112347 A | 5/2009 |
| JP | 2010035588 A | 2/2010 |
| JP | 2010220768 A | 10/2010 |
| WO | 2010109986 A1 | 9/2010 |

OTHER PUBLICATIONS

Office Action issued Jun. 30, 2014, corresponds to Chinese patent application No. 201280005675.4.

* cited by examiner

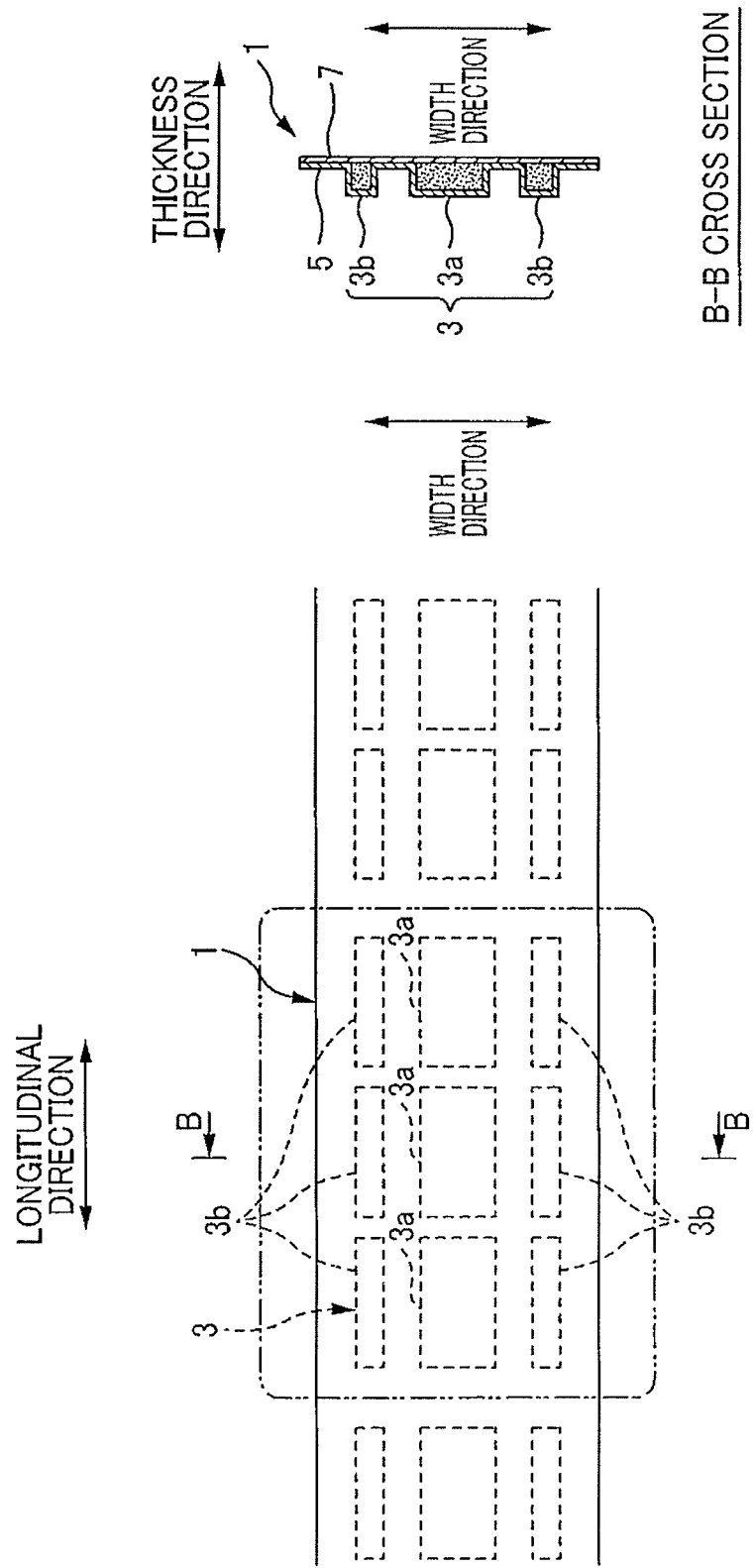

B-B ARROW VIEW

APPARATUS FOR MANUFACTURING ABSORBENT BODY

RELATED APPLICATIONS

The present application is a National Phase of PCT/JP2012/050588, filed Jan. 13, 2012, and is based on, and claims priority from, Japanese Application No. 2011-009077 filed Jan. 19, 2011.

TECHNICAL FIELD

The present invention relates to manufacturing apparatuses of an absorbent body of an absorbent article such as a disposable diaper.

BACKGROUND ART

As examples of absorbent articles that absorb liquid such as excretory fluid, there are known disposable diapers, sanitary napkins and the like. These absorbent articles normally include an absorbent body formed by molding pulp fiber into a predetermined shape, but recently there are cases where only granular superabsorbent polymer (hereinafter, referred to as "SAP") is used to form an absorbent body, without using liquid absorbent fiber such as pulp fiber.

An example of an apparatus 110 that manufactures such an absorbent body 103 is disclosed in PTL 1. FIG. 1A is a schematic perspective view showing a partially fragmented apparatus 110. FIGS. 1B to 1D are central vertical cross sectional views showing an enlarged main portion of the apparatus 110. With this apparatus 110, as shown in FIGS. 1B and 1C, SAP is intermittently dropped and supplied and laminated on a continuous sheet 105 transported in a transporting direction to form the absorbent body 103.

CITATION LIST

Patent Literature

PTL1: Patent Application Laid-open Publication No. 63-283777

SUMMARY

Technical Problem

Here, the SAP that has been dropped and supplied usually does not immediately stop in a landing position PO on the continuous sheet 105 in FIG. 1B, and bounces and the like on the continuous sheet 105 as shown in FIG. 1D and tries to scatter forward in the transporting direction over a wide range.

In the meantime, from the viewpoint of control of a lamination distribution, generation of an unintended supplying position should be prevented as much as possible, and in the case the supply of the SAP is performed intensively in a small range in the transporting direction, than in a wide range, the control of the lamination distribution will be satisfactory.

However, in the case of the above-mentioned device 110, as shown in FIG. 1D, it is configured so that the front of the regular supplying position PO is made as an open space SP110, and the SAP that has bounced on the continuous sheet 105 can scatter in any amount forward in the transporting direction. Thus, the SAP is being substantially supplied also in the open space SP 110. In other words, unintended supplying positions Pa, Pa ... have been formed in the open space SP 110, and the supply of the SAP is being performed over a wide range in the transporting direction, and as a result, the control of the lamination distribution is unsatisfactory, and it is imagined to be difficult to make the lamination distribution uniform.

This invention was made in view of the above problems, and the object is to provide an apparatus that manufactures an absorbent body by laminating liquid absorbent particles such as SAP and that can make the lamination distribution uniform.

Solution to Problem

An aspect of the invention to achieve the above advantages is an apparatus that manufactures an absorbent body by suctioning to a suction section a liquid absorbent particle that has fallen and laminating the liquid absorbent particle thereto, the apparatus including:

a suction member that has the suction section on a surface, the suction member moving the suction section along a predetermined travel path;

a cover member surrounding a predetermined range of the travel path; and a supply opening through which the liquid absorbent particle falls and is supplied toward the surface, the supply opening being included above the travel path in a space within the cover member, wherein, of the space within the cover member, a space located in a downstream side of a position of the supply opening in a direction along the travel path is divided into a first zone in which the liquid absorbent particle is suctioned to the suction section and a second zone in which the liquid absorbent particle is suctioned to the suction section, the second zone being adjacent to a downstream side of the first zone.

Other aspects of this invention will become clear from the description in this specification and appended drawings.

Advantageous Effects of Invention

With this invention, an apparatus that manufactures an absorbent body by laminating liquid absorbent particles such as SAP and that can easily make a lamination distribution uniform can be provided.

BRIEF DESCRIPTION OF DRAWINGS

FIG. 2A is a plan view of an absorbent main body 1 of a urine absorbing pad, and FIG. 2B is a B-B cross sectional view of FIG. 2A.

DESCRIPTION OF EMBODIMENTS

Figure 1A:
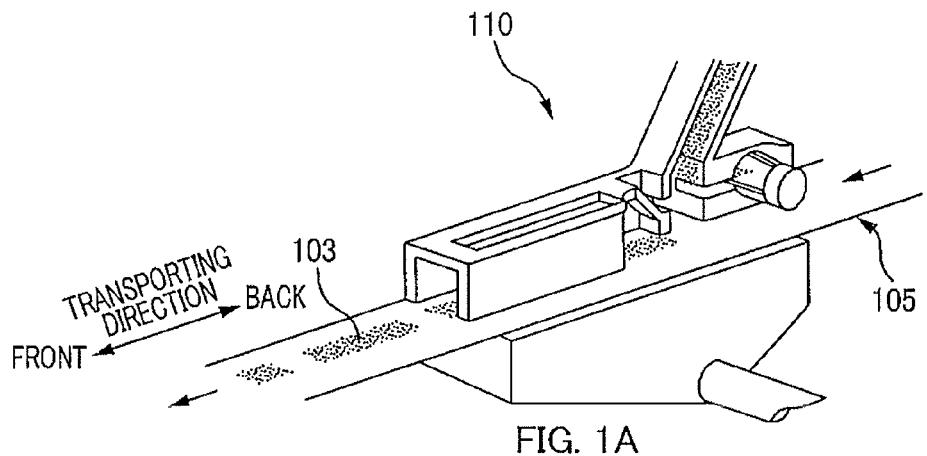
FIG. 1A is a schematic perspective view showing a part of a former manufacturing apparatus 110 of an absorbent body 103 that has been cutaway.
Figure 1B:
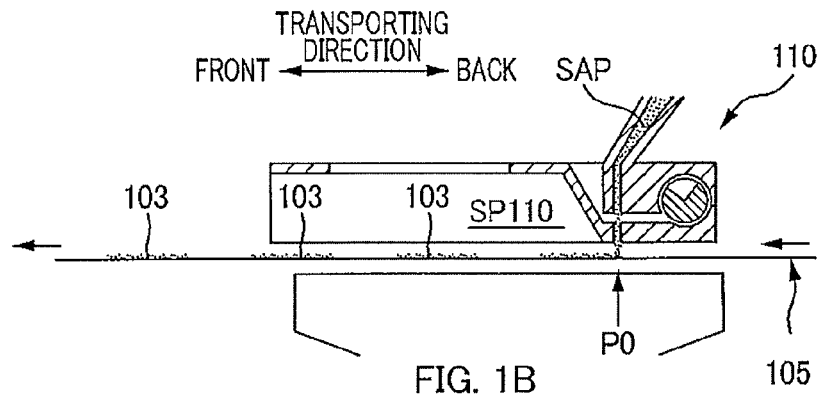
FIGS. 1B to 1D are central vertical cross sectional views showing enlarged main portions of this apparatus 110.
Figure 1C:
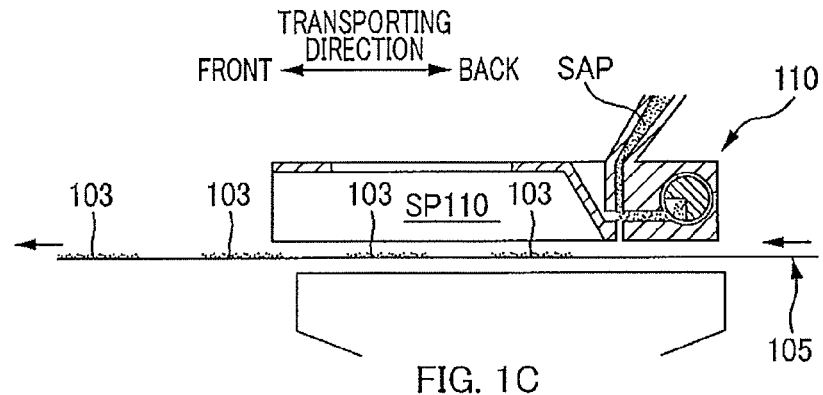
Figure 1D:
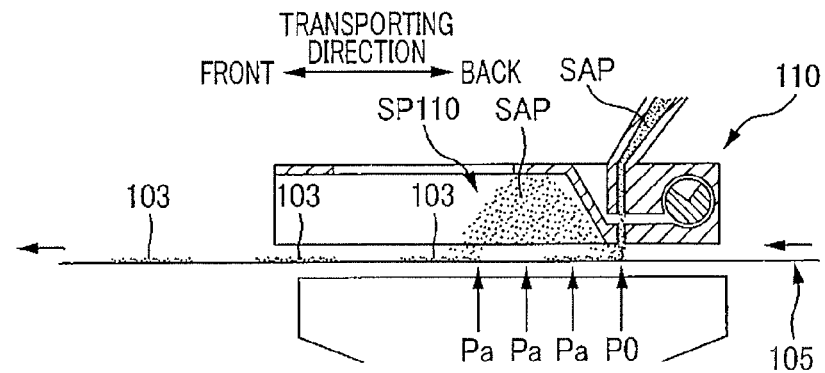

From the description in this specification and the attached drawings, at least the below matters will become clear.

An apparatus that manufactures an absorbent body by suctioning to a suction section a liquid absorbent particle that has fallen and laminating the liquid absorbent particle thereto, the apparatus including:

a suction member that has the suction section on a surface, the suction member moving the suction section along a predetermined travel path;

a cover member surrounding a predetermined range of the travel path; and a supply opening through which the liquid absorbent particle falls and is supplied toward the surface, the supply opening being included above the travel path in a space within the cover member, wherein, of the space within the cover member, a space located in a downstream side of a position of the supply opening in a direction along the travel path is divided into a first zone in which the liquid absorbent particle is suctioned to the suction section and a second zone in which the liquid absorbent particle is suctioned to the suction section, the second zone being adjacent to a downstream side of the first zone.

With such a manufacturing apparatus of the absorbent body, the space to the downstream side than the position of the supply opening in the direction along the travel path is divided into the first zone and the second zone so that the liquid absorbent particles ejected from the supply opening is substantially supplied to the suction section intensively in the first zone. Namely, compared to the case in which the space is not divided, the supply of the liquid absorbent particles to the suction section is to be performed in a small range in the direction along the travel path. Thus, improvement of control of the lamination distribution is achieved, and the lamination distribution can easily be made uniform.

Further, since the space is divided into the first zone and the second zone as described above, bouncing of the liquid absorbent particles that have dropped to the first zone on the suction section and the like and scattering to outside of the first zone can be effectively suppressed. Thus, an unintended supplying position is not made, and thus, improvement of the control of the lamination distribution can be achieved, and the lamination distribution can more easily be made uniform.

An apparatus that manufactures an absorbent body, wherein preferably by arranging a partitioning member in a boundary between the first zone and the second zone, of the space within the cover member, the space located in the downstream side of the position of the supply opening in the direction along the travel path is divided into the first zone and the second zone, scattering of the liquid absorbent particle from the first zone to the second zone is restricted with the partitioning member.

With such a manufacturing apparatus of the absorbent body, scattering of the liquid absorbent particles from the first zone to the second zone is restricted with the partitioning member. Thus, supply of the liquid absorbent particles to the suction section can be certainly achieved in the first zone, and unintended supplying positions can be certainly prevented from being made, and the lamination distribution can be easily made uniform.

An apparatus that manufactures an absorbent body, wherein preferably a second partitioning member is arranged in the second zone, the second zone is divided into an upstream side zone and a downstream side zone in the direction along the travel path with the second partitioning member.

With such a manufacturing apparatus of the absorbent body, the scattering of the liquid absorbent particles in the second zone is suppressed with the second partitioning member.

Further, leaking of the liquid absorbent particles to outside the cover member can also be suppressed.

An apparatus that manufactures an absorbent body, wherein preferably the supply opening is provided in a lower end section of a supply pipe, the liquid absorbent particle put in the supply pipe falls down the pipe of the supply pipe and is ejected from the supply opening in the lower end section, via a pipe part, included in the pipe, that decreases a falling speed of the liquid absorbent particle.

With such a manufacturing apparatus of the absorbent body, the dropping speed of the liquid absorbent particles that drop in the supply pipe is decreased in speed when passing the pipe part. Thus, after the dropping speed has decreased, the liquid absorbent particles are ejected from the supply opening of the supply pipe, and then drop to the suction section. Thus, the bouncing up of the liquid absorbent particles when landing on the suction section is suppressed, and scattering and fixing of the particles to sections other than the suction section is suppressed.

An apparatus that manufactures an absorbent body, wherein preferably the lower end section of the supply pipe includes a colliding plate against which the liquid absorbent particle that has fallen down the pipe of the supply pipe collides, the travel direction of the liquid absorbent particle is oriented to a downstream side in the direction along the travel path by colliding against the colliding plate, and the liquid absorbent particle is ejected from the supply opening.

With such a manufacturing apparatus of the absorbent body, the travel direction of the liquid absorbent particles to be ejected from the supply opening is directed to the downstream side in the direction along the travel path. Thus, the scattering of the liquid absorbent particles to the upstream side in this direction can be prevented. As a result, the supplying of the liquid absorbent particles to the suction section can be certainly performed in the first zone, and the lamination distribution can be more easily made uniform.

Further, by colliding against the colliding plate, the dropping speed of the liquid absorbent particles can be decreased, and hereafter drops to the suction section. Thus, bouncing up of the liquid absorbent particles when landing on the absorbent portion is suppressed, and the scattering of the particles can be suppressed.

An apparatus that manufactures an absorbent body, wherein preferably the suction section is included in a predetermined pitch in the direction along the travel path, the suction section has a plurality of suction regions formed intermittently in the direction along the travel path, by arranging the partitioning member in a boundary between the first zone and the second zone, the space located in the downstream side of the position of the supply opening in the direction along the travel path of the space within the cover member is divided into the first zone and the second zone, and a distance between an end edge in the downstream side in the direction along the travel path in the colliding plate and a lower end edge of the partitioning member is equal to or smaller than a length in the direction along the travel path of each of the suction regions.

With such a manufacturing apparatus of the absorbent body, the liquid absorbent particles can be supplied solidly in respect to each suction region, and the lamination distribution thereof can be made uniform.

An apparatus that manufactures an absorbent body, wherein preferably the suction section has a plurality of air-intake holes that draw in air while restricting passing through of the liquid absorbent particle, and with the drawing in of air from the air-intake holes, the liquid absorbent particle is suctioned to the suction section.

With such a manufacturing apparatus of the absorbent body, by using a simple configuration of air-intake holes, the liquid absorbent particles are to be laminated on the suction section and the absorbent body is formed, and thus the configuration of the apparatus is made simple.

An apparatus that manufactures an absorbent body, wherein preferably a wall section located to an upstream side in the direction along the travel path, of a wall section included in the cover member, is formed with an air-inlet opening that takes in air into the cover member, in a position between the air-inlet opening and the supply opening, a guide plate that guides a flow of the air taken in from the air-inlet opening to the supply opening is included, and with the guide plate the flow of the air is guided to the supply opening as a flow toward the downstream side in the direction along the travel path.

With such a manufacturing apparatus of the absorbent body, the air that has been taken in from the air-inlet opening is maintained to flow toward the downstream side in the direction along the travel path with the guide plate to reach the supply opening. Thus, the liquid absorbent particles ejected from the supply opening is blown to the downstream side, and because of this the liquid absorbent particles ejected from the supply opening can be guided certainly to the downstream side in the direction along the travel direction.

The Present Embodiment

In a manufacturing apparatus 10 of an absorbent body 3 of the present embodiment, for example, an absorbent main body 1 of a urine absorbing pad for a disposable diaper is manufactured.

The urine absorbing pad is to be used by being attached to a completed disposable diaper, and mainly absorbs liquid excretion such as urine. Then, after absorbing a predetermined amount, only this used urine absorbing pad is detached from the disposable diaper, and the diaper can be replaced with an unused urine absorbing pad.

The urine absorbing pad has an absorbent main body 1 in a substantially sheet shape that absorbs liquid excretion and that is arranged to a human body side, and a liquid non-permeable leak prevention sheet that covers the absorbent main body 1 from a surface at an opposite side to the body side and that can be adhered to this surface.

FIGS. 2A and 2B are explanatory diagrams of the absorbent main body 1. FIG. 2A is a plan view, and FIG. 2B is a cross-sectional view taken along the line B-B in FIG. 2A. It should be noted that in FIG. 2A, one unit of the absorbent main body 1 corresponding to a product of the urine absorbing pad is shown by surrounding it with a double-dotted chained line.

As shown in FIGS. 2A and 2B, a planar view of the absorbent main body 1 has a substantially rectangular shape having a longitudinal direction and a width direction. Further, the absorbent main body is a substantially three layer structure in a thickness direction. More specifically, the absorbent body 3 that absorbs the liquid is covered with a surface sheet 5 from the surface side, which is the human-body side, and is also covered with a back face sheet 7 from the back surface side, which is an opposite side. In a state of sandwiching the absorbent body 3 between the surface sheet 5 and the back face sheet 7, the surface sheet 5 and the back face sheet 7 are attached to each other in a frame-like manner in sections extending outwardly beyond four sides of the absorbent body 3 to form the absorbent main body 1.

The surface sheet 5 and the back face sheet 7 are liquid-permeable sheets having permeability, and for example, is a nonwoven fabric made of synthetic fiber and the like having a basis weight of 10 to 50 $(g/m^2)$. As a synthetic fiber, single fiber or conjugated fiber having a sheath-core structure such as polyethylene, polyethylene terephthalate and the like can be provided. It should be noted that, the back face sheet 7 may be a liquid-impermeable sheet.

The absorbent body 3 is made of particulate superabsorbent polymers having a particle diameter of 100 to 800 micrometers, for example (corresponding to a liquid-absorbent particles, hereinafter referred to as SAP), and is formed by laminating the SAP at a basis weight of 100 to 500 $(g/m^2)$. The absorbent body 3 is configured by a plurality of island-shaped laminated parts $3a$, $3b$ . . . into which the absorbent body 3 has been divided in a predetermined laminating pattern in the longitudinal direction and the width direction. In the example shown in the figures, the absorbent body 3 is divided into three parts in each of the width direction and the longitudinal direction. The absorbent body 3 includes a total of nine laminated parts $3a$, $3b$ . . . . As a specific example of SAP, UG-840D (product name: made by Sumitomo Seika Chemicals Co., Ltd.) and the like is provided.

Figure 3:
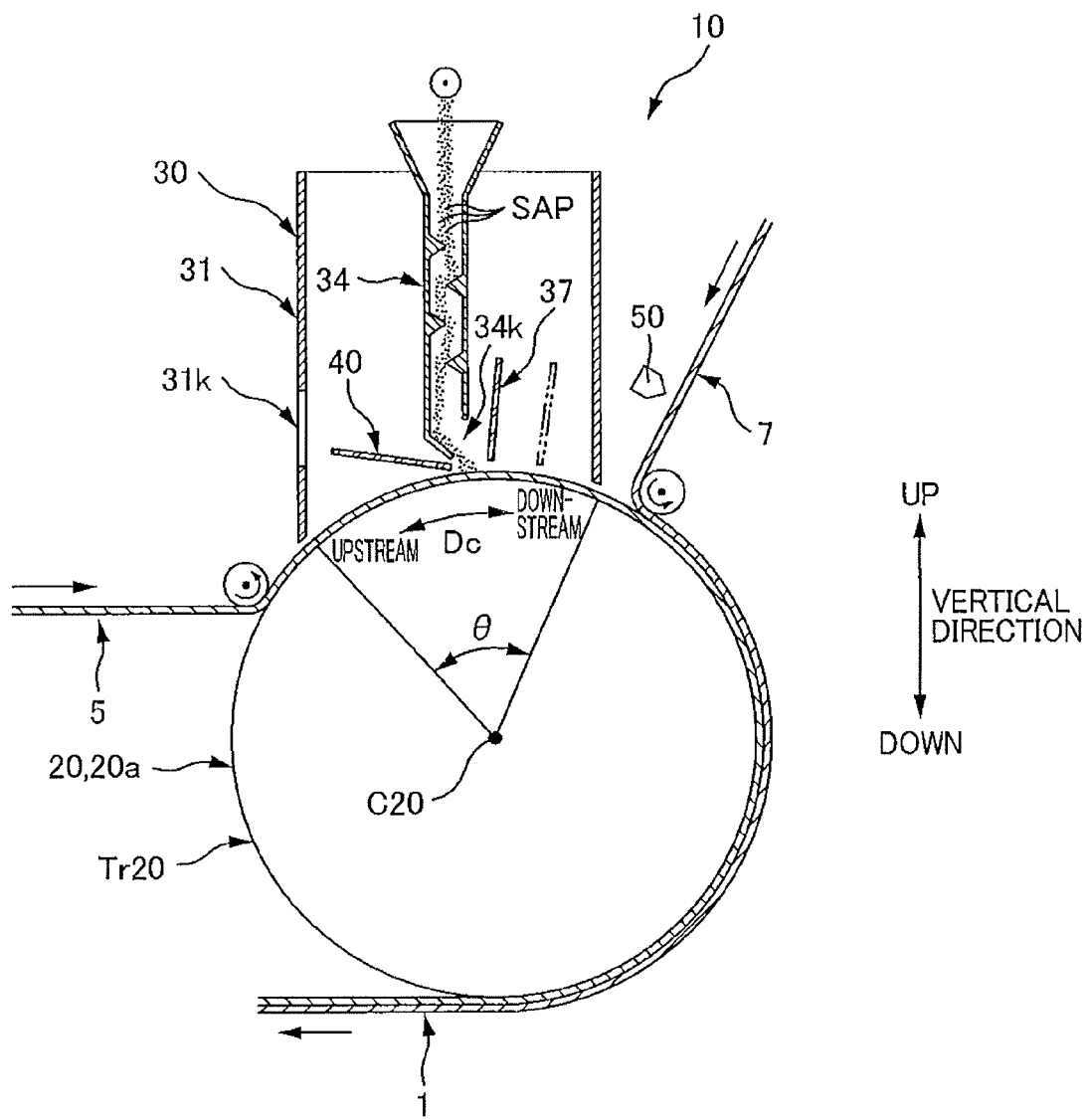
FIG. 3 is a schematic side cross sectional view of a manufacturing apparatus 10 of an absorbent body 3 of the present embodiment.

FIG. 3 is a schematic side cross sectional view of the manufacturing apparatus 10 for the absorbent main body 1. At this point in the course of manufacturing, in the same way as in FIG. 2A, the absorbent main body 1 is a continuous body that has not yet been divided into product units in the longitudinal direction. Further, the width direction of the absorbent main body 1 is aligned in the width direction of the manufacturing apparatus 10 (a direction perpendicular to the paper surface in FIG. 3). Hereinafter this width direction is referred to as a "CD direction". In this regard, the CD direction is horizontal.

This manufacturing apparatus 10 has a rotating drum 20 as a suction member. The rotating drum 20 continuously rotates so that its outer circumferential surface $20a$ (corresponds to a surface) moves along a predetermined circumferential path Tr20 (corresponds to a travel path). Further, around the circumferential surface $20a$ of the rotating drum 20 that is continuously rotating is wrapped a continuous body of the surface sheet 5 (hereinbelow, merely referred to as the surface sheet 5) at a predetermined wraparound angle, and in this way, the surface sheet 5 is transported substantially integrally with the outer circumferential surface $20a$. Then, toward the outer circumferential surface $20a$ of the rotating drum 20 that is in a state wrapped with this surface sheet 5, the SAP is dropped and supplied from the SAP supplying device 30. As a result of this, the SAP is attached over the surface sheet 5 to the suction sections 21 (not shown in FIG. 3) of the outer circumferential surface $20a$, and the absorbent body 3 is laminated. Then, finally the back face sheet is supplied to the outer circumferential surface $20a$ of the rotating drum 20, and thus the back face sheet 7 is overlapped on the surface sheet 5 that is laminated with the absorbent body 3 and joined integrally, and thus the above-mentioned continuous body of the absorbent main body 1 is manufactured.

Note that, in this example, the back face sheet 7 before being overlapped on the surface sheet 5 is applied with an adhesive such as a hot-melt adhesive with an adhesive applying device 50 in advance, and with this adhesive the above-mentioned integral joining is performed, but the method of this integral joining is not limited thereto.

Figure 4:
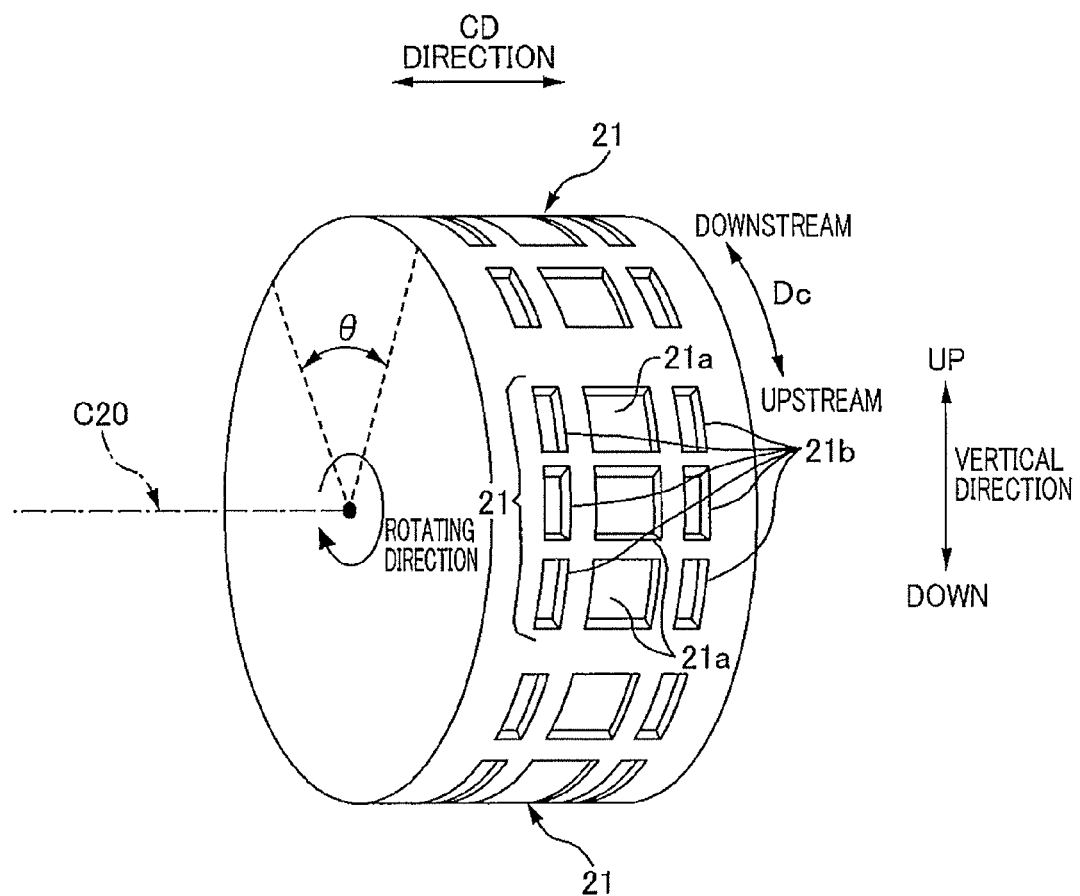
FIG. 4 is a schematic perspective view of a rotating drum 20.

FIG. 4 shows a schematic perspective view of the rotating drum 20. The main body of the rotating drum 20 is a cylindrical member that is driven and rotates about a horizontal axis C20 along the CD direction. The outer circumferential face 20a of the rotating drum 20 is horizontal with respect to the CD direction. On the outer circumferential face 20a, the molds 21 of the absorbent body 3 as the suction sections 21 are provided at a predetermined pitch in the circumferential direction Dc (corresponds to a direction along the travel path) of the rotating drum 20. Each mold 21 is formed based on the foregoing lamination pattern with a plurality of depressions 21a, 21b as suction regions; in this example each one of the molds 21 includes nine of the depressions 21a, 21b . . . , for example. A bottom section of each of the depressions 21a, 21b . . . is formed substantially horizontally in respect to the CD direction, and further a large number of air-intake holes (not shown) are formed on the bottom section. These air-intake holes are configured to take in air when passing a rotation angle range θ in which the SAP supplying device 30 (FIG. 3) has been arranged of the above-mentioned circumferential path Tr20. At that time, each air-intake hole draws in air while restricting passing of the SAP. Thereby, when the mold 21 passes the rotation angle range θ in FIG. 3, the SAP is attached and laminated over the surface sheet 5 to each of the depressions 21a, 21b . . . of the mold 21.

A configuration of an air-intake mechanism that makes the air-intake holes draw in the air in the rotation angle range θ is, for example, as follows. First, the configuration is illustrated in which the air-intake holes are configured as through holes which communicate with an inner circumferential space of the rotating drum 20, a partition wall which partitions a space corresponding to the rotation angle range θ of the inner circumferential space from other spaces is included, and further a negative pressure source such as a blower is connected to the space in order to take in the air from the space corresponding to the rotation angle range θ.

Figure 5A:
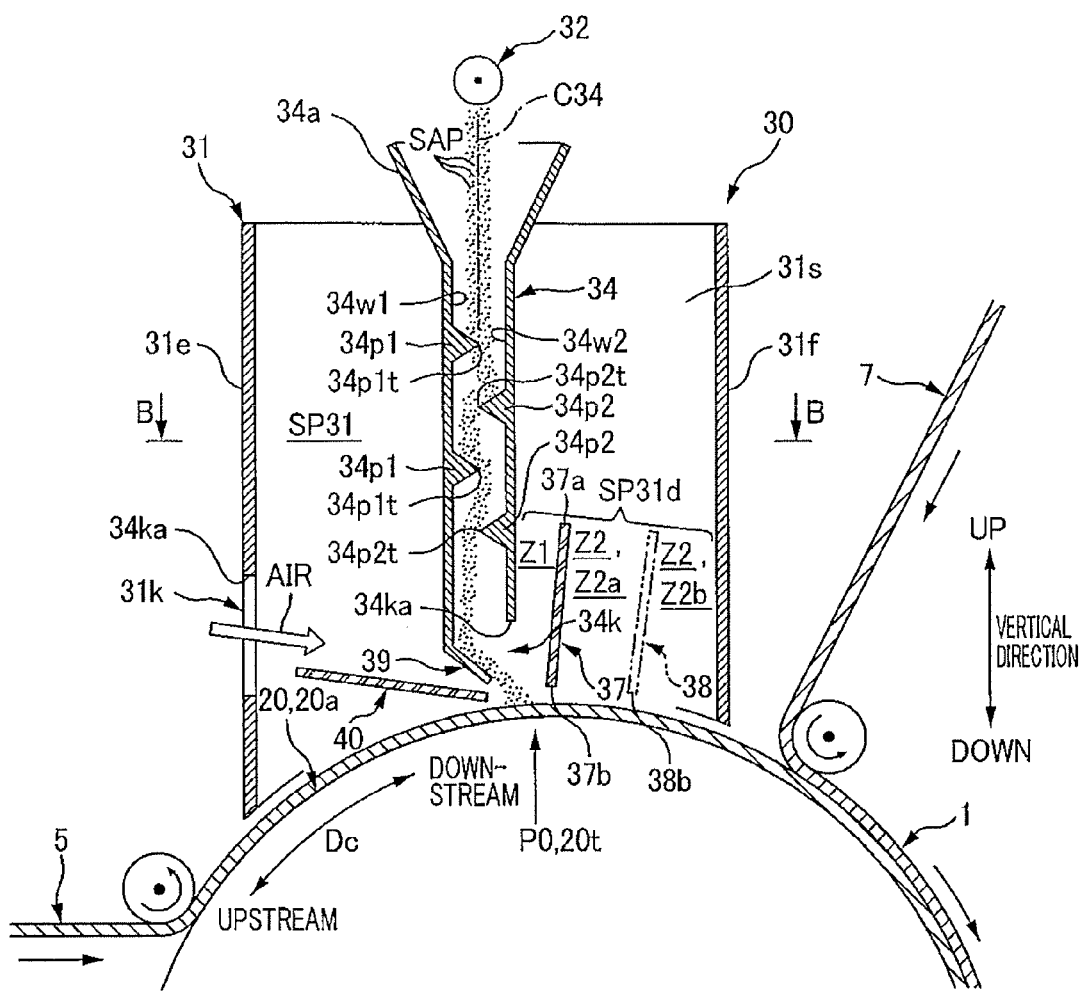
FIG. 5A is an enlarged view of a SAP supplying device 30.
Figure 5B:
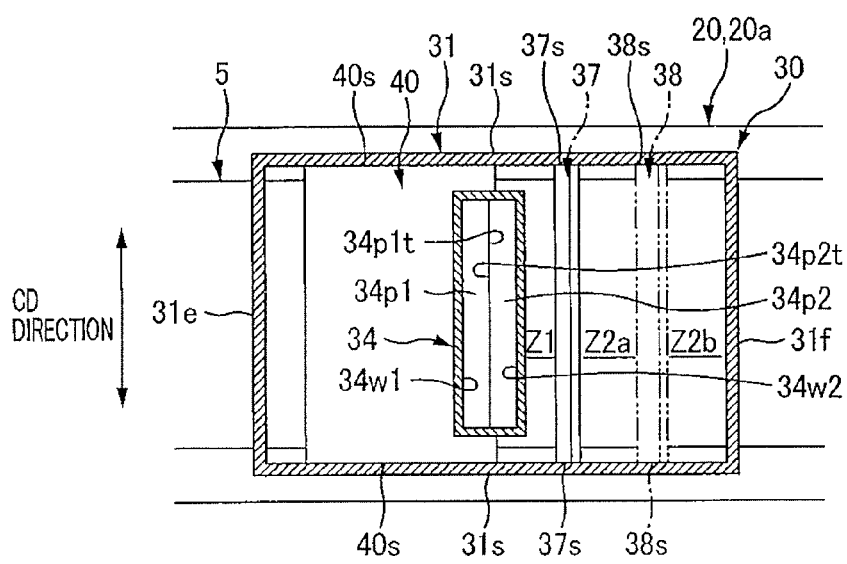
FIG. 5B is a B-B cross sectional view of FIG. 5A.

FIG. 5A is an enlarged view of the SAP supplying device 30, and FIG. 5B is a cross-sectional view taken along line B-B in FIG. 5A. The SAP supplying device 30 is placed surrounding above substantially a top 20t of the outer circumferential face 20a of the rotating drum 20. The SAP supplying device 30 includes: a surrounding member 31 (corresponds to a cover member) which, together with that outer circumferential face 20a, forms a space SP31 located above the outer circumferential face 20a; a SAP supply pipe 34 (corresponds to a supply pipe) which is almost housed in the surrounding member 31 and supplies the SAP; and a partitioning plate 37 (corresponds to a partitioning member) that divides the space SP31d downstream in the circumferential direction Dc than the position of the supply opening 34k of the SAP supply pipe 34 of the space SP31 in the surrounding member 31 into a first zone Z1 and a second zone Z2.

The surrounding member 31 is, for example, a cylindrical body (frame body) with a substantially rectangular section without an upper side wall section and a lower side wall section, and includes four wall sections 31f, 31e, 31s, 31s for the other four surfaces. The surrounding member 31 is arranged with its lower surface side being opposed to the top 20t of the outer circumferential face 20a of the rotating drum 20. Therefore, by being surrounded by the surrounding member 31, the SAP is prevented from scattering around to the periphery.

Further, on a wall section 31e to the upstream side in the circumferential direction Dc of the four wall sections 31f, 31e, 31s, 31s of the surrounding member 31, an air-inlet opening 31k is formed passing through the wall. Therefore, the air drawn in from the air-intake holes of the foregoing mold 21 is taken in from the air-inlet opening 31k into the surrounding member 31, in addition to from the upper end opening portion of the surrounding member 31. This air-inlet opening 31k will be described later.

The SAP supply pipe 34 is a pipe member with its pipe axial direction C34 facing substantially in the up-down direction as a whole, and here a square pipe with a rectangular cross section is used. In an upper end portion thereof, a funnel portion 34a is provided in communication with a pipe of the SAP supply pipe 34, and in a lower end section thereof the supply opening 34k is formed open and in communication with the pipe. The funnel portion 34a protrudes above the surrounding member 31. Then, above the funnel portion 34a is provided a screw feeder 32 that feeds the SAP in a fixed quantity, and the SAP is dropped and supplied from the screw feeder 32 to the funnel portion 34a in a substantially uniform distribution in the CD direction. Then, the SAP is dropped down the pipe of the SAP supply pipe 34 and ejected from the supply opening 34k in the lower end section, and thus the SAP is supplied to substantially the top 20t of the outer circumferential surface 20a of the rotating drum 20 or in the periphery thereof. Note that, with the SAP supply pipe 34, several ideas have been performed such as a part of the pipe is made in a zigzag state, and such ideas will be described later.

The partitioning plate 37 is arranged in a space SP 31d to the downstream side in the circumferential direction Dc than a position of the supply opening 34k of the space SP31 in the surrounding member 31, in order to make the lamination distribution of the SAP uniform.

Namely, as described above, when the space to which the SAP is to be ejected from the supply opening 34k of the SAP supply pipe 34 (space to the downstream side directly near the supply opening 34k in the circumferential direction Dc) is too large, the SAP that has been dropped and supplied does not immediately stop in a landing position on the surface sheet 5 on the rotating drum 20, and bounces or the like on the surface sheet 5 and scatters in a wide area toward the downstream side in the circumferential direction Dc. Then, with this scattering, in effect, the supplying position to which the SAP is to be supplied toward the surface sheet 5 is increased to a plurality of locations that was not intended from the one place of the regular position PO. As a result, forming of the absorbent body 3 with a uniform lamination distribution becomes difficult. Further, in the case the supply of the SAP is performed intensively and solidly in a small area in the circumferential direction Dc than in a wide area, control of the lamination distribution becomes satisfactory and the lamination distribution can easily be made uniform.

Thus, in this embodiment, by providing a partitioning plate 37, the space SP31d in the downstream side in the circumferential direction Dc than the supply opening 34k is divided into a first zone Z1 and a second zone Z2 adjacent to the downstream side of the first zone Z1. As a result, bouncing of the SAP, that has dropped in the first zone Z1, on the surface sheet 5 on the rotating drum 20 and scattering out of the first zone Z1 is suppressed, and thus generation of unintended supplying positions is suppressed. Further, the size of the adjoining space (referring to the first zone Z1) of the supply opening 34k is made narrower by this division, so that the SAP can be supplied solidly to the surface sheet 5 on the rotating drum 20 in a narrow range. Then, from the above, the controlling of the lamination distribution can be improved, and the distribution can easily be made uniform.

The partitioning plate 37 is arranged so that its upper end edge 37a is in a position higher than the upper end edge 34ka of the supply opening 34k, and the lower end edge 37b is arranged opposing the surface sheet 5 with a predetermined clearance therebetween. Then, the clearance between the lower end edge 37b and the upper surface of the surface sheet 5 is set to, for example, 3 mm to 5 mm. In this way, while avoiding interference of the lower end edge 37b with the surface sheet 5, and suppressing a large difference in pressure to the front and back (upstream and downstream) of the partitioning plate 37, the amount of the SAP that passes the clearance and scatters to the second zone Z2 can be effectively suppressed.

This partitioning plate 37 is, for example, a rectangular plate, and, as shown in FIG. 5B, the surrounding member 31 is fixedly supported to a pair of side wall sections 31s, 31s included in both ends of the surrounding member 31 in the CD direction. Namely, to the pair of side wall sections 31s, 31s of the surrounding member 31, both end edges 37s, 37s in the CD direction of the partitioning plate 37 are fixed so as to come in contact with no clearance. Also in this way, scattering of the SAP to the second zone Z2 is suppressed.

As shown in FIG. 5A, preferably, a similar partitioning plate 38 (corresponds to a second partitioning member) is separately provided also in respect to the second zone Z2, and as a result of this, the second zone Z2 can be divided into a zone Z2a in the upstream side in the circumferential direction Dc and a zone Z2b in the downstream side. If that happens, the scattering of the SAP in the second zone Z2 can be suppressed with the partitioning plate 38. Further, the leaking out of the SAP to outside the surrounding member 31 can be suppressed. It should be noted that, this partitioning plate 38 is also a rectangular flat plate, similar to the above-described partitioning plate 37, and further the clearance between the lower end edge 38b and the upper surface of the surface sheet 5 is set to 3 mm to 5 mm, for example, and furthermore both end edges 38s, 38s in the CD direction of the partitioning plate 38 is supported fixedly in contact with and without a clearance to the pair of side wall sections 31s, 31s of the surrounding member 31 (FIG. 5B). It should be noted that, by providing two or more of the partitioning plates 38, the second zone Z2 can be divided into three or more zones.

By the way, in this embodiment, other than the above-mentioned partitioning plates 37, several ideas have been performed to make the lamination distribution of the SAP uniform, and it is described as below.

First, as one idea, as shown in FIG. 5A, a portion of the pipe of the SAP supply pipe 34 is made into a zigzag form. For this reason, the SAP that is placed into the SAP supply pipe 34 via the funnel portion 34a collides or the like against an inner wall surface of the pipe portion in the zigzag form, thus decreasing the dropping speed, and thereafter the SAP is ejected from the supply opening 34k in the lower end section of the supply pipe 34, and falls on the surface sheet 5 on the rotating drum 20. Namely, this pipe portion in the zigzag form has a function to decrease the dropping speed of the SAP. Thus, based on this decrease in speed, the bouncing up of the SAP when landing on the surface sheet 5 is suppressed, and as a result the scattering of the SAP is suppressed.

The forming of this pipe portion in the zigzag shape is achieved by using, for example, a straight pipe with a linear pipe axial direction C34 as a main body of the SAP supply pipe 34, and forming protruding sections 34p1, 34p2 . . . in a staggered manner to the pair of inner wall surfaces 34w1, 34w2 opposing each other in the straight pipe.

For example, in the example in FIG. 5A, the inner wall surface 34w1 to the upstream side in the circumferential direction Dc of the straight pipe is formed with a plurality of protruding sections 34p1, 34p1 in a predetermined pitch in the pipe axial direction C34, and further the inner wall surface 34w2 to the downstream side is formed with a plurality of protruding sections 34p2, 34p2 in the pipe axial direction C34, and further the position in which the protruding section 34p1 is formed on the inner wall surface 34w1 to the upstream side and the position in which the protruding section 34p2 is formed on the inner wall surface 34w2 to the downstream side are shifted for a half of the predetermined pitch in the pipe axial direction C34. Therefore, a portion of the pipe of the SAP supply pipe 34 is formed in a zigzag state.

Here, preferably, the position of the top 34p1t of the protruding section 34p1 on the inner wall surface 34w1 to the upstream side and the position of the top 34p2t of the protruding section 34p2 of the inner wall surface 34w2 to the downstream side, can be made to match each other in the circumferential direction Dc or can be made to overlap each other in the circumferential direction Dc. In this way, the collision rate of the SAP dropping down the pipe against the protruding sections 34p1, 34p2 is increased, and the dropping speed of the SAP can be certainly decreased. Incidentally, in the example in FIG. 5A, the position of the top 34p1t of the protruding section 34p1 on the inner wall surface 34w1 to the upstream side and the position of the top 34p2t of the protruding section 34p2 on the inner wall surface 34w2 to the downstream side are made to match each other in the circumferential direction Dc.

Further, in the illustrated figure, the vertical cross sectional shapes of the protruding sections 34p1, 34p2 are made as a triangular shape, but it is not limited thereto, and the shape may be a polygon such as a rectangle or a trapezoid, and further may even be a circular shape. Incidentally, this vertical cross sectional shape is maintained in the same shape over the entire width in the CD direction, and in this way the lamination distribution of the SAP in the CD direction can be made uniform.

As a second idea, a colliding plate 39 against which the SAP that has dropped down the pipe collides is provided to the lower end section of the SAP supply pipe 34, and further with the collision of the SAP to this colliding plate 39, the orientation of the colliding plate 39 is adjusted so that the travel direction of the SAP is directed toward the downstream side in the circumferential direction Dc and ejected from the supply opening 34k. Accordingly, first, the dropping speed of the SAP is further decreased by the collision to the colliding plate 39, and as a result, when the SAP lands on the surface sheet 5 the bouncing up of the SAP is suppressed. Further, the travel direction of the SAP to be ejected from the supply opening 34k is directed to the downstream side in the circumferential direction Dc, so that the scattering of the SAP to the upstream side in the circumferential direction Dc can be certainly prevented. As a result, the supply of the SAP to the surface sheet 5 is performed in almost only the first zone Z1, and thus the lamination distribution can be more easily made more uniform.

Incidentally, the direction of the colliding plate 39 is set in the following direction in order to make the colliding plate 39 function as mentioned-above. That is, as shown in an enlarged view of the main parts in FIG. 6, the colliding plate 39 is arranged inclined in an inclination angle θ 39 of for example 35 to 45 degrees in respect to the horizontal direction, with the end edge 39d in the downstream side in the circumferential direction Dc of the colliding plate 39 positioned lower than the end edge 39u in the upstream side.

Further, the clearance between the end edge 39d to the downstream side in the circumferential direction Dc which is a lower end edge of the colliding plate 39 and the upper surface of the surface sheet 5 is set to 1 mm to 5 mm, for example. In this way, the interference between the colliding plate 39 and the surface sheet 5 can be effectively avoided. Note that, in this example, the end edge 39d to the downstream side of the colliding plate 39 can be said to configure the lower end edge of the supply opening 34k.

Figure 6:
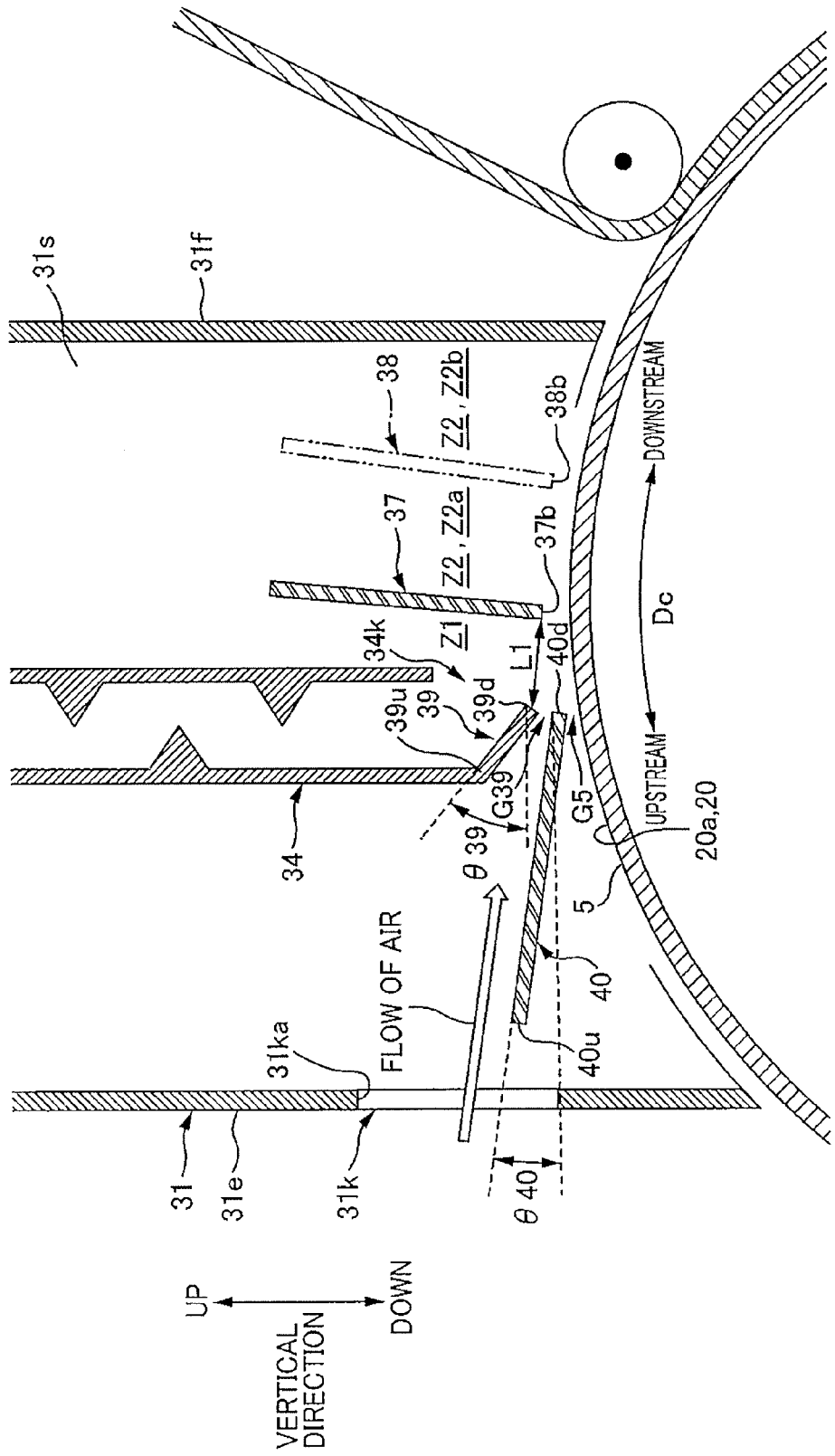
FIG. 6 is an enlarged view of main parts of the SAP supplying apparatus 30.

Further, preferably, as shown in FIG. 6, a length L1 in the circumferential direction Dc of the substantially lower end section of the first zone Z1, namely, a distance L1 between the lower edge 39d to the downstream side in the circumferential direction Dc of the colliding plate 39 and the lower end edge 37b of the partitioning plate 37 is set equal to or smaller than a length in the circumferential direction Dc of the depressions 21a, 21b . . . of the mold 21. Here, in the case the length in the circumferential direction Dc of the depressions 21a, 21b . . . in FIG. 4 has a plurality of sizes, the above-mentioned distance L1 is set equal to or smaller than a minimum value of the plurality of sizes. In this way, the SAP can be solidly supplied in respect to each of the depressions 21a, 21b . . . , and the lamination distribution can be made uniform.

As a third idea, as shown in FIG. 5A, an air-inlet opening 31k to take in air into the surrounding member 31, is formed penetrating through the wall section 31e to the upstream side in the circumferential direction Dc of the wall sections 31f, 31e, 31s, 31s of the surrounding member 31, and further in the position between the air-inlet opening 31k and the supply opening 34k of the SAP supply pipe 34 is provided a guide plate 40 that guides the flow of air taken in from the air-inlet opening 31k to the supply opening 34k. In this way, the air taken in from the air-inlet opening 31k reaches the supply opening 34k while maintaining the flow directed to the downstream side in the circumferential direction Dc, and the SAP ejected from the supply opening 34k is scattered to the downstream side. As a result, the SAP to be ejected from the supply opening 34k can be guided certainly to the downstream side in the circumferential direction Dc.

This guide plate 40 is for example a flat plate, and both end edges 40s, 40s in the CD direction are fixedly supported to come in contact with the pair of side wall sections 31s, 31s of the surrounding member 31 without a clearance (FIG. 5B).

Further, the orientation of the guide plate 40 is set in the following orientation. Namely, as shown in FIG. 6, the guide plate 40 is arranged inclined with an inclination angle θ 40 of for example 5 to 15 degrees in respect to the horizontal direction, so that the end edge 40d to the downstream side in the circumferential direction Dc of the guide plate 40 is positioned lower than the end edge 40u to the upstream side. At that time, the position of the end edge 40u to the upstream side of the guide plate 40 in the up-down direction is arranged to be positioned lower than the upper end edge 31ka of the air-inlet opening 31k, the end edge 40d to the downstream side of the guide plate 40 is arranged interposed in a position between the colliding plate 39 and the surface sheet 5 on the rotating drum 20, and the end edge 40d is arranged in between both the colliding plate 39 and the surface sheet 5 separating the intervals G39, G5 (FIG. 6). Thus, the air taken in from the air-inlet opening 31k is guided to the upper surface of the guide plate 40 and flows to the downstream side in the circumferential direction Dc, and then promptly reaches the supply opening 34k by passing the interval G39 in between the colliding plate 39 and the guide plate 40.

Other Embodiments

Embodiments of the present invention have been described as above, however the present invention is not limited to these embodiments and the following variations are also possible.

In the foregoing embodiment, the rotating drum 20 is illustrated as the suction member. However, the invention is not limited thereto. For example, it is possible to use a belt of a belt conveyor as the suction member, to form the molds 21 as the suction sections with a plurality of depressions on the belt, and to move the belt along a predetermined track as the travel path.

In the above embodiment, as the suction section, the mold 21 having a plurality of depressions 21a, 21b . . . is illustrated, but the suction section does not have to be formed as depressions. For example, the suction sections can be formed by only forming a plurality of air-intake holes, in a flat predetermined region on the outer circumferential face 20a of the rotating drum 20.

In the above embodiment, as the liquid absorbent particles, the superabsorbent polymers (SAP) are illustrated, but it is not limited to superabsorbent polymers, as long as they are particles that have a characteristic that does not release absorbed liquid by swelling and the like.

In the above-mentioned embodiment, the surface sheet 5 is wrapped around the outer circumferential surface 20a of the rotating drum 20, and the absorbent body 3 is formed by suctioning and laminating the SAP in the mold 21 on the outer circumferential surface 20a over the surface sheet 5, but it is not limited thereto. For example, the absorbent body 3 can be formed by directly suctioning the SAP to the mold 21 on the outer circumferential surface 20a, without wrapping the surface sheet 5 around the outer circumferential surface 20a of the rotating drum 20.

In the above embodiment, in order to provide a pipe part that decreases the falling speed of the SAP in the pipe of the SAP supply pipe 31, a plurality of protrusions 34p1, 34p2, are provided on the inner wall surface of the SAP supply pipe 31, but the number of the protrusions 34p1, 34p2, is not limited to several, but may be one.

REFERENCE SIGNS LIST 1 absorbent main body,
3 absorbent body,
3a laminated part,
3b laminated part,
5 surface sheet,
7 back face sheet,
10 manufacturing apparatus,
20 rotating drum (suction member),
20a outer circumferential face (surface),
20t roughly top,
21 mold (suction section),
21a depression (suction region),
21b depression (suction region),
30 SAP supplying device,
31 surrounding member (cover member),
31e wall section,
31f wall section,
31s side wall section,
31k air-inlet opening,
31ka upper end edge,
32 screw feeder,
34 SAP supply pipe (supply pipe),
34a funnel portion,
34k supply opening, 34*ka* upper end edge,
34*p*1 protruding section,
34*p*1*t* top,
34*p*2 protruding section,
34*p*2*t* top,
34*w*1 inner wall surface,
34*w*2 inner wall surface,
37 partitioning plate (partitioning member),
37*a* upper end edge,
37*b* lower end edge,
37*s* end edge,
38 partitioning plate (second partitioning member),
38*b* lower end edge,
38*s* end edge,
39 colliding plate,
39*d* end edge,
39*u* end edge,
40 guide plate,
40*d* end edge,
40*s* end edge,
40*u* end edge,
50 adhesive applying apparatus,
SP31 space in surrounding member (space in cover member),
SP31*d* space in downstream side,
Tr20 circumferential path (travel path),
Dc circumferential direction (direction along travel path),
Z1 first zone,
Z2 second zone,
Z2*a* upstream side zone,
Z2*b* downstream side zone,
C20 horizontal axis,
G5 interval,
G39 interval

The invention claimed is:

1. An apparatus that manufactures an absorbent body by suctioning to a suction section a liquid absorbent particle that has fallen and laminating the liquid absorbent particle thereto, the apparatus comprising:
a suction member that has the suction section on a surface, the suction member moving the suction section along a predetermined travel path;
a cover member surrounding a predetermined range of the travel path; and
a supply opening through which the liquid absorbent particle falls and is supplied toward the surface, the supply opening being included above the travel path in a space within the cover member,
wherein, of the space within the cover member, a space located in a downstream side of a position of the supply opening in a direction along the travel path is divided into a first zone in which the liquid absorbent particle is suctioned to the suction section and a second zone in which the liquid absorbent particle is suctioned to the suction section, the second zone being adjacent to a downstream side of the first zone,
wherein the suction section has a plurality of air-intake holes that draw in air while restricting passing through of the liquid absorbent particle, and
with the drawing in of air from the air-intake holes, the liquid absorbent particle is suctioned to the suction section,
wherein a wall section located to an upstream side in the direction along the travel path, of a wall section included in the cover member, is formed with an air-inlet opening that takes in air into the cover member,
in a position between the air-inlet opening and the supply opening, a guide plate that guides a flow of the air taken in from the air-inlet opening to the supply opening is included, and with the guide plate the flow of the air is guided to the supply opening as a flow toward the downstream side in the direction along the travel path.

2. An apparatus according to claim 1, further comprising a partitioning member in a boundary between the first zone and the second zone, of the space within the cover member so that the space located in the downstream side of the position of the supply opening in the direction along the travel path is divided by the partitioning member into the first zone and the second zone,
wherein the partitioning member is configured to restrict scattering of the liquid absorbent particle from the first zone to the second zone.

3. An apparatus according to claim 2, further comprising a second partitioning member arranged in the second zone,
wherein the second zone is divided into an upstream side zone and a downstream side zone in the direction along the travel path with the second partitioning member.

4. An apparatus according to claim 1, further comprising a supply pipe including a pipe and a pipe part included in the pipe,
wherein
the supply opening is provided in a lower end section of the supply pipe,
the supply pipe is configured such that the liquid absorbent particle put in the supply pipe falls down the pipe of the supply pipe and is ejected from the supply opening in the lower end section, via the pipe part, and
the pipe part is configured to decrease a falling speed of the liquid absorbent particle.

5. An apparatus according to claim 4, further comprising:
at the lower end section of the supply pipe, a colliding plate configured to cause the liquid absorbent particle that has fallen down the supply pipe collides,
wherein the colliding plate is further configured to orient the travel direction of the liquid absorbent particle to the downstream side in the direction along the travel path by colliding against the colliding plate so that the liquid absorbent particle is ejected from the supply opening.

6. An apparatus according to claim 5, wherein
the suction section is included in a predetermined pitch in the direction along the travel path,
the suction section has a plurality of suction regions formed intermittently in the direction along the travel path,
the apparatus further includes a partitioning member in a boundary between the first zone and the second zone, the space located in the downstream side of the position of the supply opening in the direction along the travel path of the space within the cover member is divided by the partitioning member into the first zone and the second zone, and
a distance between an end edge in the downstream side in the direction along the travel path in the colliding plate and a lower end edge of the partitioning member is equal to or smaller than a length in the direction along the travel path of each of the suction regions.

7. An apparatus for manufacturing an absorbent body by suctioning and laminating liquid absorbent particles in a suction section, the apparatus comprising:
a suction member having, on a surface thereof, the suction section, the suction member configured to move the suction section along a predetermined travel path;
a cover member surrounding a predetermined range of the travel path; and
a supply opening through which the liquid absorbent particles fall and are supplied toward the surface, the supply opening being included above the travel path and in a space within the cover member, wherein the space within the cover member includes a space section located in a downstream side of a position of the supply opening in a direction along the travel path, the space section is divided into a first zone in which the liquid absorbent particles are suctioned to the suction section and a second zone in which the liquid absorbent particles are suctioned to the suction section, the second zone being adjacent to a downstream side of the first zone, the suction section has a plurality of air-intake holes configured to draw in air while restricting passing of the liquid absorbent particles through the plurality of air-intake holes, the suction section is configured to suck the liquid absorbent particles by the air drawn in from the air-intake holes, the cover member includes a wall section located to an upstream side in the direction along the travel path, the wall section formed with an air-inlet opening configured to take in air into the cover member, the apparatus further comprises, in a position between the air-inlet opening and the supply opening, a guide plate configured to guide a flow of the air taken in from the air-inlet opening to the supply opening, and the guide plate is configured to guide the flow of the air to the supply opening as a flow toward the downstream side in the direction along the travel path.

* * * * *